United States Patent [19]

Balinth

[11] 4,147,831

[45] Apr. 3, 1979

[54] PRESSURE-SENSITIVE ADHESIVE COMPOSITIONS

[75] Inventor: Ivan J. Balinth, Cranford, N.J.

[73] Assignee: Johnson & Johnson, New Brunswick, N.J.

[21] Appl. No.: 829,376

[22] Filed: Aug. 31, 1977

[51] Int. Cl.$^2$ ............................ C09J 3/12; C09J 3/14; A61L 15/06

[52] U.S. Cl. ................................... 428/356; 128/156; 260/4 R; 260/27 R; 260/888; 428/492; 428/496; 428/498; 428/537

[58] Field of Search ............... 428/492, 496, 356, 498, 428/537; 128/156; 260/4 R, 888, 27 R

[56] References Cited

U.S. PATENT DOCUMENTS

| | | | |
|---|---|---|---|
| 2,177,627 | 10/1939 | Drew | 428/356 |
| 2,251,273 | 8/1941 | Drew | 428/496 |
| 2,328,066 | 8/1943 | Drew | 428/356 |
| 2,358,761 | 9/1944 | Reed | 428/356 |
| 2,429,223 | 10/1947 | Eustis | 428/356 |
| 2,534,883 | 12/1950 | Smyers | 428/496 |
| 2,744,041 | 5/1956 | Balchen | 428/496 |
| 2,909,278 | 10/1959 | Blackford | 428/356 |
| 2,971,863 | 2/1961 | Kindseth | 428/356 |
| 3,212,925 | 10/1965 | Rosenthal | 428/356 |
| 4,061,826 | 12/1977 | Petras | 428/356 |

Primary Examiner—Ellis P. Robinson
Attorney, Agent, or Firm—Steven P. Berman

[57] ABSTRACT

Pressure-sensitive adhesive compositions having improved adhesion characteristics in water comprising an elastomeric mixture consisting of natural rubber and polyisobutylene, a liquid plasticizer component and a solid tackifier component.

6 Claims, No Drawings

PRESSURE-SENSITIVE ADHESIVE COMPOSITIONS

BACKGROUND OF THE INVENTION

This invention relates to adhesive compositions. More particularly, this invention relates to pressure-sensitive adhesive compositions suitable for use in the preparation of adhesive bandages, adhesive tapes, adhesive sheet materials and the like, which provide excellent adhesive characteristics when adhered to a part of the body and do not significantly lose said characteristics when immersed in or exposed to water.

This invention also relates to surgical sheet materials such as adhesive tapes and to adhesive bandages and dressings, such as coverings for cuts, abrasions and the like, which comprise a flexible backing member, one of whose major surfaces has adhered thereto a coating of the pressure-sensitive adhesives of the present invention.

Various types of pressure-sensitive adhesives have been proposed and utilized as the adhesive component in adhesive bandages, adhesive tapes and the like. Acrylate polymers, polyolefinic polymers and compounded systems based on natural or synthetic rubber polymers have all been tried or utilized as pressure-sensitive adhesives with varying degrees of success.

A pressure-sensitive adhesive must have certain characteristics to be useful. It must be sufficiently tacky, i.e., have sufficient "grab" or "quick-stick", to adhere quickly to the surface to which it is to be adhered. It must also continue to adhere to that surface over extended periods of time. A pressure-sensitive adhesive composition should also have sufficient internal strength to prevent splitting and leaving particles of adhesive on a surface to which an article coated with the adhesive has been adhered when the article is removed. Where the pressure-sensitive adhesive is designed for application to the skin, the problems of adherence are substantially increased. Although the initial tack or stick may be good, adherence over an extended period of time for many pressure-sensitive adhesives is found to be relatively poor whether because of movement of the underlying skin or the nature of the underlying skin surface as where perspiration and other surface changes may occur. The problem is further complicated by the fact that any pressure-sensitive adhesive designed for application to the skin must release from the skin sufficiently readily to permit removal without skin damage. Where the adhesive is too strongly adhered to the skin and has substantial internal strength, small particles of the upper layer of skin are removed with the adhesive with resulting irritation to the skin. As a result, although many pressure-sensitive adhesives are available for various commercial uses, relatively few have been found which are suitable for articles for skin applications.

A particularly important and desirable characteristic of a pressure-sensitive adhesive designed for application to the skin is its adhesion time when worn in or exposed to water. The failure of adhesive bandages, adhesive tapes and the like to adequately hold when immersed in or exposed to water, such as washing dishes, doing laundry, swimming or the like, has long been an undesirable problem.

SUMMARY OF THE INVENTION

It is an object of this invention to provide improved pressure-sensitive adhesive compositions.

It is a further object of the present invention to provide pressure-sensitive adhesive compositions which exhibit good adhesion time when utilized in water.

It is a still further object of the present invention to provide adhesive bandages, adhesive tapes and the like which exhibit good adhesion characteristics when utilized in water.

Other objects and advantages of the present invention will be readily available to one skilled in the art from the following description.

The foregoing objects and other features and advantages of the present invention are achieved by a pressure-sensitive adhesive composition comprising a specific elastomeric mixture, a liquid plasticizer component and a solid tackifier component in specific amounts as well as the normal fillers, antioxidants, stabilizers, plasticizers, extenders and the like normally utilized in such pressure-sensitive adhesive compositions.

DETAILED DESCRIPTION OF THE INVENTION

A pressure-sensitive adhesive composition is provided by the present invention which comprises from about 30% to about 50% of an elastomeric mixture consisting of natural rubber and polyisobutylene, from about 5% to about 20% of a liquid plasticizer component and from about 30% to about 50% of a solid tackifier component.

The term "natural rubber" as used in describing this invention includes both the naturally occurring form of rubber, i.e., cis-1,4-polyisoprene, as well as synthetically prepared cis-1,4-polyisoprene.

The elastomeric mixture of the adhesive composition of the present invention should be from about 30% to about 50% by weight of the total composition, preferably from about 34% to about 40% by weight to achieve the desired results. The elastomeric mixture gives the adhesive composition its pressure-sensitive adhesive characteristics and high temperature stability. This high temperature stability permits the sterilization of the products, such as adhesive bandages, to which the adhesive composition is applied. For example, if an adhesive composition utilized cis-1,4-polyisoprene alone as the elastomeric component, upon the application of the temperatures normally used for sterilization, the adhesive would flow and oxidation would occur resulting in degradation of the adhesive and therefore its undesirability.

The elastomeric mixture of the present invention consists of natural rubber and polyisobutylene in a ratio by weight of from about 1:1 to about 3:1. If the mixture contains more than about 50% polyisobutylene, the resulting adhesive composition will exhibit excess adhesiveness and possibly result in skin trauma upon removal and if the mixture contains less than about 25% polyisobutylene, the resulting adhesive composition will be difficult to sterilize since the mixture will flow at the termperatures normally utilized for sterilization.

As discussed above, the natural rubber of the elastomeric mixture can be either the naturally occurring or the synthetically prepared cis-1,4-polyisoprene. The natural rubber of the elastomeric mixture gives the resulting composition its tackiness and aids in the "quick-stick" to the skin. The polyisobutylene of the elastomeric mixture must be of a molecular weight of from about 64,000 to about 99,000, preferably about 81,000 to 99,000 or mixtures of molecular weights within said ranges. These molecular weight ranges are determined by the Staudinger viscosity method. If a polyisobutylene of a molecular weight less than 64,000 is utilized, the resulting adhesive composition will be too soft and will leave particles adhered to the skin upon removal. Further, the resulting compositions would tend to flow at the temperatures normally utilized for sterilization, i.e., 160° F. and above. If a polyisobutylene of a molecular weight greater than 99,000 is utilized, then the performance of the resultant adhesive compositions in water would be undesirably affected.

The liquid plasticizer component of the pressure-sensitive adhesive compositions of the present invention should be from about 5% to about 20% by weight of the total composition, preferably about 8% to about 14% by weight to achieve the desired results. The liquid plasticizer component controls the tackiness of the adhesive compositions and can be selected from the group consisting of isomeric liquid polybutenes; mineral oils; low molecular weight polyterpenes such as the polyterpene sold under the trademark Wingtack 10 by Goodyear Chemical Company, the polyterpenes sold under the trademarks Piccolyte S-55 and Piccolyte A-40 by Hercules Chemical Company, and the polyterpene sold under the trademark Zonarez 25 by Arizona Chemical Company; and low viscosity rosins such as the low viscosity rosin sold under the trademark Stabelite Ester #3 by Hercules Chemical Company; and mixtures thereof. When mineral oils are utilized as the liquid plasticizer component, they shoud comprise no more than 50% of the liquid plasticizer component to avoid any loss of adhesive characteristics and they should therefore be combined with one of the other abovementioned liquid plasticizers.

The solid tackifier component of the adhesive compositions of the present invention should be from about 30% to about 50% by weight of the total composition, preferably from about 38% to about 48% by weight to achieve the desired results. The solid tackifier component assists in plasticizing the elastomeric mixture to give the desired bonding and adhesive characteristics. A solid tackifier rather than a liquid tackifier must be utilized because a liquid tackifier results in an adhesive composition which is too soft for its intended uses.

The solid tackifier component should exhibit a softening point of between 100° C. and 125° C. to be useful in the pressure-sensitive adhesive compositions of the present invention. If the solid tackifier component has a softening point less than 100° C., the resulting adhesive composition will not exhibit satisfactory adhesiveness, particularly the desired properties in water. If the solid tackifier component has a softening point above 125° C., the resulting adhesive compositions may cause skin damage upon removal. The solid tackifier component can be selected from the group consisting of normally solid polyterpenes, solid rosins and mixtures thereof. Specific normally solid polyterpenes which are useful include a normally solid polyterpene sold under the trademark Piccolyte S115 by Hercules Chemical Company, a normally solid polyterpene sold under the trademark Wingtack 115 by Goodyear Chemical Company, a normally solid polyterpene sold under the trademark Escorez 115 by Exxon Chemical Company, and normally solid polyterpenes sold under the trademarks Nirez 1115 and Nirez 1125 by Reichhold Chemical Company. Specific solid rosin tackifiers include those sold under the trademarks Pentalyn A and Polypale Ester No. 10 by Hercules Chemical Company.

If desired, the pressure-sensitive adhesive compotions of the present invention can include fillers, extenders, antioxidants, stabilizers, plasticizers, color pigments and other ingredients known in the art for inclusion in such compositions. The fillers can be added as extenders or cost-reducing agents, as reenforcing agents or as color and pigment agents and can be present in the composition from about 0 to about 10% by weight, preferably from about 2% to about 7% by weight of the total composition.

The extenders can include finely divided clays, bentonites, carbonates such as calcium carbonate, diatomaceous earth, starches or other inert ingredients normally used in adhesive compositions. The reenforcing agents include silicas and various oxides such as zinc oxide. The coloring agents or pigments can include titanium dioxide, carbon black, iron oxides and the like.

Antioxidants and stabilizers can be utilized at levels of from about 1% to 3% by weight of the total composition, preferably from about 1% to 2%. Suitable antioxidants and stabilizers include butyl zimate, 2,6-di-tert-butyl-4 methyl phenol sold under the trademark Ionol by Shell Chemical Company; 2,5-di(tert-amyl)hydroquinone sold under the trademark Santowar A by Monsanto Chemical Company; a mixture of alkylated diphenylamines sold under the trademark Agerite Stalite by Vanderbilt Chemical Company, and the like. These stabilizers and antioxidants give improved shelf life characteristics and prevent degredation of the pressure-sensitive adhesive compositions of the present invention.

It has further been found that to obtain pressure-sensitive adhesive compositions with the desired characteristics including the improved water adhesion time, it is necessary for such compositions to have a Williams plasticity measurement of from about 1.5mm to about 2.4mm, preferably about 1.8mm to about 2.2mm. If the Williams plasticity is below 1.5mm, the adhesive compositions will be too soft and exhibit undesirable flow as well as remaining adhered to the skin upon removal. If the Williams plasticity is above 2.4mm, the adhesive compositions will be too hard and exhibit poor tackiness.

In the preparation of pressure-sensitive surgical sheet materials for application to the skin, such as pressure-sensitive adhesive tapes, adhesive bandages, surgical drapes and the like, the pressure-sensitive adhesive compositions of the present invention are coated onto a flexible backing material in accordance with known techniques. Suitable flexible backing materials include polymeric films, paper, woven and nonwoven fabrics or other similar flexible sheet materials.

Specific embodiments of the present invention are illustrated by the following examples. It will be understood, however, that the present invention is not confined to the specific limitations set forth in the individual examples, but rather to the scope of the appended claims.

EXAMPLES

EXAMPLE I

A pressure-sensitive adhesive composition is prepared by placing 160 pounds of natural rubber and 58 pounds of polyisobutylene of a molecular weight range of from 64,000 to 81,000 in a Banbury mixer for a period of five minutes. Thereafter, 50 pounds of isomeric liquid polybutenes are added over a period of ten minutes while maintaining the temperature between 220° F. and 290° F. The resultant mixture is placed on a two-roll sheeter mill manufactured by the Farrel-Birmingham Company. The temperature of the rolls is adjusted to 200° F. and mixing is commenced for a period of five minutes. Thereafter, 250 pounds of a solid tackifier such as Wingtack 115 are added and the temperature is raised to 250° F. on the front roll and 300° F. on the back roll for a period of ten minutes to produce a pressure-sensitive adhesive of the following composition:

|  | % By Weight |
|---|---|
| Natural Rubber | 30.89 |
| Polyisobutylene | 11.20 |
| Isomeric Liquid Polybutenes | 9.65 |
| Solid Tackifier | 48.26 |
|  | 100.00 |

EXAMPLE II

A pressure-sensitive adhesive composition is prepared substantially in accordance with the process of EXAMPLE I and having the following composition:

|  | By Weight |
|---|---|
| Natural Rubber | 28.00 |
| Polyisobutylene (mol. wt. 81,000-99,000) | 10.10 |
| Filler | 4.60 |
| Iosmeric Liquid Polybutenes | 8.74 |
| Mineral Oils | 2.80 |
| Antioxidants | 2.06 |
| Solid Tackifier | 43.70 |
|  | 100.00 |

This adhesive composition is suitable for coating on a suitable baking. This coating can be accomplished by techniques well-known in the art such as calendering, extrusion deposition via organic solutions and the like.

EXAMPLE III

A pressure-sensitive adhesive composition is prepared substantially in accordance with the process of EXAMPLE I and having the following composition:

|  | % By Weight |
|---|---|
| Natural Rubber | 28.12 |
| Polyisobutylene (mol. wt. 81,000-99,000) | 10.19 |
| Isomeric Liquid Polybutenes | 7.03 |
| Fillers | 5.28 |
| Titanium Dioxide Pigment | 0.88 |
| Antioxidants | 1.05 |
| Liquid Plasticizer | 1.76 |
| Mineral Oils | 1.76 |
| Wingtack 115 | 43.93 |
|  | 100.00 |

This pressure-sensitive adhesive composition is suitable for coating on a suitable backing. The coating can be accomplished by techniques well-known in the art such as calendering, extrusion, deposition via organic solutions and the like.

EXAMPLES IV-VII

Four pressure-sensitive adhesive compositions were prepared substantially in accordance with the process of EXAMPLE I and had the following general composition:

|  | % By Weight |
|---|---|
| Natural Rubber | 28.00 |
| Polyisobutylene | 10.10 |
| HiSil 233 Filler | 4.60 |
| Isomeric Liquid Polybutenes | 8.74 |
| Primol 355 Mineral Oil | 2.80 |
| Agerite Stalite | 1.03 |
| Ionol | 1.03 |
| Wingtack 115 | 43.70 |
|  | 100.00 |

The four compositions differed only in the molecular weight ranges of the polyisobutylene as follows:

|  | Mol. Wt. Ranges Polyisobutylene |
|---|---|
| EXAMPLE IV | 64,000-81,000 |
| EXAMPLE V | 81,000-99,000 |
| EXAMPLE VI | 99,000-117,000 |
| EXAMPLE VII | 117,000-135,000 |

These pressure-sensitive adhesive compositions were coated by means of calender coating techniques on a vinyl plastic backing with an absorbent pad to form an adhesive bandage. These bandages were then applied to the middle three fingers of 30 individuals who then placed their hands in a dishwashing solution consisting of a commercial dishwashing product mixed with hot water. The fingers were flexed in the dishwashing solution for a period of fifteen minutes and then withdrawn and the adhesive performance ranked according to the Friedman Statistical Ranking Test. The resultant statistical data has been converted to a rating system of excellent, good, fair and poor. The ratings for the molecular weight ranges are summarized below in Table I.

Table I

| Example | Mol. Wt. Ranges Polyisobutylene | Rating |
|---|---|---|
| IV | 64,000-81,000 | Excellent |
| V | 81,000-99,000 | Excellent |
| VI | 99,000-117,000 | Fair |
| VII | 117,000-135,000 | Fair |

The results show that as the molecular weight range of polyisobutylene goes outside the range of 64,000-99,000 of the adhesive compositions of the present invention, the performance characteristics in water of the resulting adhesive compositions are unsatisfactory.

EXAMPLE VII

Utilizing the same dishwashing test of EXAMPLES IV-VII, the adhesive composition of EXAMPLE V was compared with commercially available adhesive bandages and ranked in accordance with the same procedure as in EXAMPLES IV-VII. The results are reported below in TABLE II.

Table II

| Product | Rating |
|---|---|
| EXAMPLE V | Excellent |
| Commercial Product A | Good |
| Commercial Product B | Good |

Table II-continued

| Product | Rating |
|---|---|
| Commercial Product C | Fair |
| Commercial Product D | Fair |

As can be noted from the above results, the adhesive composition of EXAMPLE V exhibited superior in-water characteristics when compared with four commercially available products.

EXAMPLES IX–X

Two pressure-sensitive adhesive compositions were prepared substantially in accordance with the process of EXAMPLE I and had the following general composition:

|  | % By Weight |
|---|---|
| Natural Rubber | 28.00 |
| Polyisobutylene (mol. wt. 81,000–99,000) | 10.10 |
| HiSil Filler | 4.60 |
| Isomeric Liquid Polybutenes | 8.74 |
| Primal 355 Mineral Oil | 2.80 |
| Agerite Stalite | 1.03 |
| Ionol | 1.03 |
| Solid Tackifier | 43.70 |
|  | 100.00 |

The two compositions differed only in the softening point of the solid tackifier. EXAMPLE IV used a Wingtack 115 and EXAMPLE X used a Wingtack 95, i.e., 115° C. and 95° C., respectively, for the softening points.

Utilizing the same dishwashing test and procedure of ranking of EXAMPLES IV–VII, the adhesive composition of EXAMPLE IX was compared with the adhesive composition of EXAMPLE X and the results are shown in Table III below:

Table III

| Example | Solid Tackifier Softening Point | Rating |
|---|---|---|
| IX | 115° C. | Excellent |
| X | 95° C. | Good |

This demonstrates the effect of changes in the softening point of the solid tackifier component on the in-water adhesion characteristics of the adhesive compositions of the present invention.

EXAMPLE XI

Utilizing a so-called "swim test," the adhesive composition of EXAMPLE V was compared with various commercial products. The "swim test" was conducted by applying adhesive bandages containing a pressure-sensitive adhesive composition to the mid-backs of thirty individuals who then swam for a period of fifteen minutes in a swimming pool. The bandages were then ranked for adhesion characteristics and the swimmers then swam for two additional periods of fifteen minutes with the bandages being further ranked at the end of each period. The results are reported below in Table IV in accordance with the ranking procedure of EXAMPLES IV–VII:

Table IV

|  | Rating |
|---|---|
| EXAMPLE V | Excellent |
| Commercial Product A | Good |
| Commercial Product B | Good |
| Commercial Product C | Good |
| Commercial Product D | Good |
| Commercial Product E | Fair |
| Commercial Product F | Good |
| Commercial Product G | Good |

As can be noted from the above results, the adhesive composition of EXAMPLE V exhibited superior in-water adhesion characteristics when compared with seven commercially available products.

What is claimed is:

1. A pressure-sensitive adhesive composition comprising from about 30% to about 50% by weight of the total composition of an elastomeric mixture consisting of natural rubber and polyisobutylene wherein the polyisobutylene has a molecular weight range of from about 64,000 to about 99,000, from about 5% to about 20% by weight of the total composition of a liquid plasticizer component, and from about 30% to about 50% by weight of the total composition of a solid tackifier component having a softening point of from about 100° C. to about 125° C., wherein the elastomeric mixture of natural rubber and polyisobutylene is in a ratio of from about 1:1 to about 3:1 and the composition has a Williams plasticity of from about 1.5mm to about 2.4mm.

2. A composition according to claim 1 wherein the polyisobutylene has a molecular weight range of from about 81,000 to about 99,000.

3. A composition according to claim 1 wherein the liquid plasticizer component is selected from the group consisting of isomeric liquid polybutenes, mineral oils, low molecular weight polyterpenes, low viscosity rosins and mixtures thereof, with the proviso that when mineral oil is utilized, it comprises no more than 50% of the liquid plasticizer component.

4. A composition according to claim 1 wherein the solid tackifier component is selected from the group consisting of normally solid polyterpenes, solid rosins and mixtures thereof.

5. A composition according to claim 1 wherein there is included materials selected from the group consisting of fillers, antioxidants, stabilizers, plasticizers, color pigments and mixtures thereof.

6. A surgical pressure-sensitive adhesive product comprising a flexible backing having a pressure-sensitive adhesive composition coated on at least one side thereof, said pressure-sensitive adhesive composition comprising from about 30% to about 50% of an elastomeric mixture consisting of natural rubber and polyisobutylene wherein the polyisobutylene has a molecular weight range of from about 64,000 to about 99,000, from about 5% to about 20% by weighting of the total composition of a liquid plasticizer component, and from about 30% to about 50% by weight of the total composition of a solid tackifier component having a softening point of from about 100° C. to about 125° C., wherein the elastomeric mixture of natural rubber and polyisobutylene is in a ratio of from about 1:1 to about 3:1 and the pressure-sensitive adhesive composition has a Williams plasticity of from about 1.5 mm to about 2.4 mm.

* * * * *